United States Patent
Bernard et al.

(10) Patent No.: US 12,178,621 B2
(45) Date of Patent: Dec. 31, 2024

(54) FAST AND LOW MEMORY USAGE CONVOLUTIONAL NEURAL NETWORK FOR TOMOSYNTHESIS DATA PROCESSING AND FEATURE DETECTION

(71) Applicant: GE Precision Healthcare LLC, Wauwatosa, WI (US)

(72) Inventors: Sylvain Bernard, Montigny le Bretonneux (FR); Vincent Bismuth, Paris (FR)

(73) Assignee: GE Precision Healthcare LLC, Wauwatosa, WI (US)

( * ) Notice: Subject to any disclaimer, the term of this patent is extended or adjusted under 35 U.S.C. 154(b) by 515 days.

(21) Appl. No.: 17/667,764

(22) Filed: Feb. 9, 2022

(65) Prior Publication Data
US 2023/0248323 A1    Aug. 10, 2023

(51) Int. Cl.
A61B 6/02 (2006.01)
A61B 6/50 (2024.01)
G06T 7/00 (2017.01)
G06T 11/00 (2006.01)
G16H 30/40 (2018.01)

(52) U.S. Cl.
CPC ............ *A61B 6/025* (2013.01); *A61B 6/502* (2013.01); *G06T 7/0008* (2013.01); *G06T 11/006* (2013.01); *G16H 30/40* (2018.01); *G06T 2207/20084* (2013.01); *G06T 2207/30068* (2013.01); *G06T 2207/30096* (2013.01)

(58) Field of Classification Search
CPC ....... A61B 6/025; A61B 6/502; G06T 7/0008; G06T 11/006; G06T 2207/20084; G06T 2207/30068; G06T 2207/30096; G06T 2207/10081; G06T 2207/30004; G06T 7/0012; G16H 30/40; G06N 3/084; G06V 10/82
USPC ......................................................... 382/128
See application file for complete search history.

(56) References Cited

U.S. PATENT DOCUMENTS

| | | | |
|---|---|---|---|
| 10,092,262 B2 | 10/2018 | Bernard | |
| 2016/0189376 A1* | 6/2016 | Bernard | A61B 6/502 382/132 |
| 2018/0114312 A1* | 4/2018 | Palma | G06T 11/005 |
| 2020/0211240 A1* | 7/2020 | Bernard | G06T 11/008 |

(Continued)

FOREIGN PATENT DOCUMENTS

FR    2967520 B1    12/2012

OTHER PUBLICATIONS

EP application 23153862.0 filed Jan. 30, 2023—extended Search Report issued Jul. 7, 2023; 9 pages.

(Continued)

*Primary Examiner* — Juan A Torres
(74) *Attorney, Agent, or Firm* — Boyle Fredrickson S.C.

(57) ABSTRACT

A convolutional neural network (CNN) is employed in an automated feature and/or anomaly detection system for analyzing images provided by X-ray imaging system. The automated detection system operates in a manner that reduces the number of full-resolution CNN convolution layers required in order to speed up the network inference and learning processes for the detection system. To do so, the detection system utilizes as an input a more compact representation of the tomographic data to alleviate the CNN memory footprint and computation time issues in prior art X-ray systems.

21 Claims, 9 Drawing Sheets

(56) References Cited

U.S. PATENT DOCUMENTS

| | | | | |
|---|---|---|---|---|
| 2020/0311923 | A1* | 10/2020 | Walton | G06T 3/18 |
| 2020/0388021 | A1* | 12/2020 | Song | G06N 3/045 |
| 2021/0097737 | A1* | 4/2021 | Kim | G06T 11/006 |
| 2021/0177371 | A1* | 6/2021 | Wang | A61B 90/39 |
| 2022/0318998 | A1* | 10/2022 | Fukuda | G06T 7/0012 |
| 2023/0023042 | A1* | 1/2023 | Bernard | G06N 3/084 |

OTHER PUBLICATIONS

Ruiz Alejandro Rodriguez: "Artificial Intelligence & Tomosynthesis for Breast Cancer Detection", Doctoral dissertation, Radboud University Nijmegen, Mar. 26, 2019 (Mar. 26, 2019), pp. 1-255, XP093058567, Retrieved from the Internet:URL:https://core.ac.uk/download/pdf/200780406.pdf [retrieved on Jun. 28, 2023].

Akshat C. Pujara et al., "Digital Breast Tomosynthesis Slab Thickness: Impact on Reader Performance and Interpretation Time", Dec. 2020, https://pubs.rsna.org/doi/epdf/10.1148/radiol.2020192805.

Jonas Adler et al., "Task adapted reconstruction for inverse problems", Sep. 2018, https://www.researchgate.net/publication/327386527_Task_adapted_reconstruction_for_inverse_problems.

Kaichao Liang et al., "Comparision of projection domain, image domain, and comprehensive deep learning for sparse-view X-ray CT image reconstruction", Apr. 2018, https://www.researchgate.net/publication/324492446_Comparision_of_projection_domain_image_domain_and_comprehensive_deep_learning_for_sparse-view_X-ray_CT_image_reconstruction.

* cited by examiner

FAST AND LOW MEMORY USAGE CONVOLUTIONAL NEURAL NETWORK FOR TOMOSYNTHESIS DATA PROCESSING AND FEATURE DETECTION

FIELD OF THE DISCLOSURE

The present disclosure relates to the field of tomosynthesis and to a method and system for processing tomosynthesis imaging data for obtaining enhanced images and automated detection of features, lesions and/or other abnormalities in the images.

BACKGROUND OF THE DISCLOSURE

X-ray imaging systems have become a valuable tool in medical applications such as for the diagnosis of many diseases. As standard screening for breast cancer mammography 2-dimensional (2D) x-ray images are taken across the entire breast tissue. These known 2D mammograms are limited by tissue superimposition. That is to say, lesions may be masked by the tissue above or underneath, or normal structures may mimic a lesion. In order to minimize limitations of standard 2D-mammography caused by tissue superimposition, digital breast tomosynthesis using digital receptors has been developed.

The tomosynthesis systems employ at least one x-ray tube, which is moved in an arc above a stationary detector. In digital breast tomosynthesis (DBT) the volume information of an object of interest can be derived from a series of images, known as 2D projection images or projections, which are taken at various angles by means of one or more x-ray sources. From the 2D projection images, 3D volumes of varying thicknesses can be generated from the projection image data in a tomosynthesis reconstruction process for review. The generated 3D volumes offer advantages to overcome the limitations associated with tissue superimposition.

The analysis of the 3D volumes of the object of interest and diagnosis of any abnormalities represented in the 3D volumes has traditionally been performed by the operator of the imaging system or by a clinician reviewing the reconstructed 3D volume. However, as the experience of the reviewing physician often has a significant role in the accurate determination of any abnormalities in the 3D volume being reviewed, there can be differences in the diagnoses of a particular 3D volume depending upon the experience level of the particular physician reviewing the 3D volume.

In order to limit or minimize issues with the review of tomosynthesis-generated 3D volumes, various types of automated anomaly or lesion detection systems have been employed with X-ray imaging systems. The automated detection systems utilize predetermined parameters or standards in a review of each reconstructed 3D volume in order to provide objective and repeatable results for these detection processes. The automated detection systems can employ algorithms or artificial intelligence (AI) that process and/or analyze the data within the 3D volumes to provide the function of the detection of the anomalies in the 3D volume.

With regard to the types of AI that are currently employed in these X-ray imaging systems, it has been found that various deep learning/neural networks perform very well for visual recognition in essentially any vision task. Beyond the outstanding success there, neural networks pre-trained on large-scale datasets (e.g. ImageNet databases) constitutes powerful visual descriptors ("Deep Features", DFs), which are the core building block for reaching state-of-the-art performances for these neural networks in performing a particular vision task.

However, when utilizing a neural network for the analysis of tomosynthesis 2D slices or 3D volume data, unlike ImageNet data which is composed of a 2D image having 224*224 pixels, 2D mammography images are typically comprised of 2394*2850 pixels. Further, the groups of reconstructed 2D tomosynthesis images/slices are composed of an average of 50 times more data than the 2D mammography images. Therefore, when these 2D tomographic images are analyzed by a neural network as an automated detection system, this large gap in terms of data creates both significant memory footprint and computation time issues when training and applying the neural network on full field digital mammography (FFDM)/digital breast tomosynthesis (DBT) data to provide the automatic anomaly detection and/or identification function.

In particular, when implementing a convolutional neural network (CNN) to handle the analysis of a 3D tomosynthesis volume, the huge amount of data to be processed creates a significant choke point in the analysis process for the 3D volume. For an average 5 cm breast thickness that is imaged by the imaging system, the reconstructed 3D volume for the that thickness is composed of 50*2394*2850 voxels, that is 50 layered 2D images or slices each having 2394*2850 pixels. Knowing that the first layer of the CNN computes convolutions on full resolution data, i.e., the 50*2394*2850 voxels, this computation operation is a significant and time-consuming step. However, the extracting and/or identification of features, i.e., abnormalities or lesions, within full resolution images of the breast is key to capture details as close to the limits of the detector resolution as possible, such as microcalcifications or mass spicules.

Further, computation time is not the only burden when implementing CNN on tomosynthesis data. As each layer of the CNN involves extracting multiple features, these need to be stored within the system, at least temporarily. The memory footprint necessary of the temporary storage of each of these layers can then be problematic when dealing with tomosynthesis data. Even with a smart implementation that can allocate the memory when processing a given layer of the CNN, and subsequently releasing the memory once the layer is no longer useful to the ongoing analysis process, the size of the required memory footprint can still be problematic.

Therefore, it is desirable to develop an improved system and method for employing a deep learning (DL) neural network, such as a CNN, in the identification of anomalies in 2D images and/or a 3D tomosynthesis volume that significantly decreases the computational time and memory requirements for the operation of the CNN.

SUMMARY OF THE DISCLOSURE

According to one aspect of an exemplary embodiment of the disclosure, an X-ray imaging system incorporates a CNN in an automated feature and/or anomaly detection system forming a part of the X-ray imaging system. The automated detection system operates in a manner that reduces the number of full-resolution CNN convolutions required in order to speed up the network inference and learning processes for the detection system. To do so, the detection system utilizes as an input a more compact representation of the tomographic data to alleviate the CNN memory footprint and computation time issues described previously.

More specifically, in an exemplary embodiment, the compact data representation input to the CNN comprises a limited number of acquired projections, reconstructed slices, reconstructed slabs, synthetic 2D images, or combinations thereof generated from the tomosynthesis imaging procedure as compared to the total number of reconstructed slices generated by the tomosynthesis imaging procedure. For example, on a conventional DBT system, the number of projections is on average more than 5 times less than the number of reconstructed slices/planes. In the operation of the automated detection system incorporating the CNN, the linear reconstruction process for producing the slices/planes from the projection data is considered to be highly similar to a filtered backprojection (FBP) and can be utilized in the CNN, such that filtered slices/planes can be obtained by first filtering the projections and then performing the backprojection to obtain the filtered slices. Swapping the reconstruction+convolution sequence to a convolution+reconstruction sequence allows a reduction in the number of convolutions to a multiple of the number of projections instead of the total number of slices/planes. In particular, the CNN performs a filtering convolution layer on the projections to form the filtered projections, which is then followed by a reconstruction layer to form the filtered slices from the filtered projections, rather than performing convolutions directly on each of the precomputed tomographic 2D slices. This approach not only provides a benefit on the speed of operation for the computational side for the same exact output due to the significant reduction in the number of convolutions performed, but also it has a potential for increased performance. For example, supplying the CNN with projections allows the application of non-linear activations, such as a rectified linear activation function or ReLU, on the filtered projections that would have not been possible when performing convolutions on precomputed slices.

According to another exemplary aspect of the present disclosure, the learning process for the CNN can then backpropagate the filter kernels, weights and/or gradients through the reconstruction process, i.e., through the filtered slices and filtered projections, back to the convolutional kernels applied on the input projections in order to find the optimal filters for the envisioned task, e.g., anomaly detection and/or identification. The reconstruction process can be fixed using a standard back-projection process when knowing the system geometry, e.g., the positions of the X-ray source relative to the detector. In another exemplary embodiment, the reconstruction process can embed some parameters to be learned during the network training phase to assist in the envisioned task.

According to still another aspect of an exemplary embodiment of the disclosure, a method for detecting an anomaly in one or more images obtained from an X-ray imaging procedure on an object, including the steps of providing an X-ray imaging system having an X-ray source configured to emit radiation beams towards the object, a fixed X-ray detector or movably aligned with the X-ray source to receive the radiation beams from the X-ray source and generate image data, a processing unit operably connected to the X-ray source and the X-ray detector to control the movement and operation of the X-ray source and X-ray detector, the processing unit configured to receive and process image data from the X-ray detector, a display operably connected to the processing unit for presenting information to a user, a user interface operably connected to the processing unit to enable user input to the processing unit, an automatic anomaly detection system operably connected to the pro-cessing unit, and an electronic information storage device operably connected to the processing unit, obtaining a set of projection images of an object of interest, supplying a compact data representation input of the projection images to the automatic anomaly detection system, analyzing the compact data representation input with the automatic anomaly detection system to obtain an anomaly detection result, and outputting an anomaly detection result from the automatic anomaly detection system.

According to still another aspect of an exemplary embodiment of the present disclosure, an X-ray imaging system includes an X-ray source configured to emit radiation beams towards the object, a fixed X-ray detector or movably aligned with the X-ray source to receive the radiation beams from the X-ray source and generate image data, a processing unit operably connected to the X-ray source and the X-ray detector to control the movement and operation of the X-ray source and X-ray detector, the processing unit configured to receive and process image data from the X-ray detector, a display operably connected to the processing unit for presenting information to a user, a user interface operably connected to the processing unit to enable user input to the processing unit, an automatic anomaly detection system operably connected to the controller, and an electronic information storage device operably connected to the processing unit, wherein the automatic anomaly detection system is configured to receive a compact data representation input of the projection images to the automatic anomaly detection system and to analyzing the compact data representation input to obtain an anomaly detection result These and other exemplary aspects, features and advantages of the invention will be made apparent from the following detailed description taken together with the drawing figures.

BRIEF DESCRIPTION OF THE DRAWINGS

The drawings illustrate the best mode currently contemplated of practicing the present invention.

In the drawings.

DETAILED DESCRIPTION OF THE DRAWINGS

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments. As used herein, the terms "substantially," "generally," and "about" indicate conditions within reasonably achievable manufacturing and assembly tolerances, relative to ideal desired conditions suitable for achieving the functional purpose of a component or assembly. Also, as used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present. The term "real-time," as used herein, means a level of processing responsiveness that a user senses as sufficiently immediate or that enables the processor to keep up with an external process.

Figure 1:
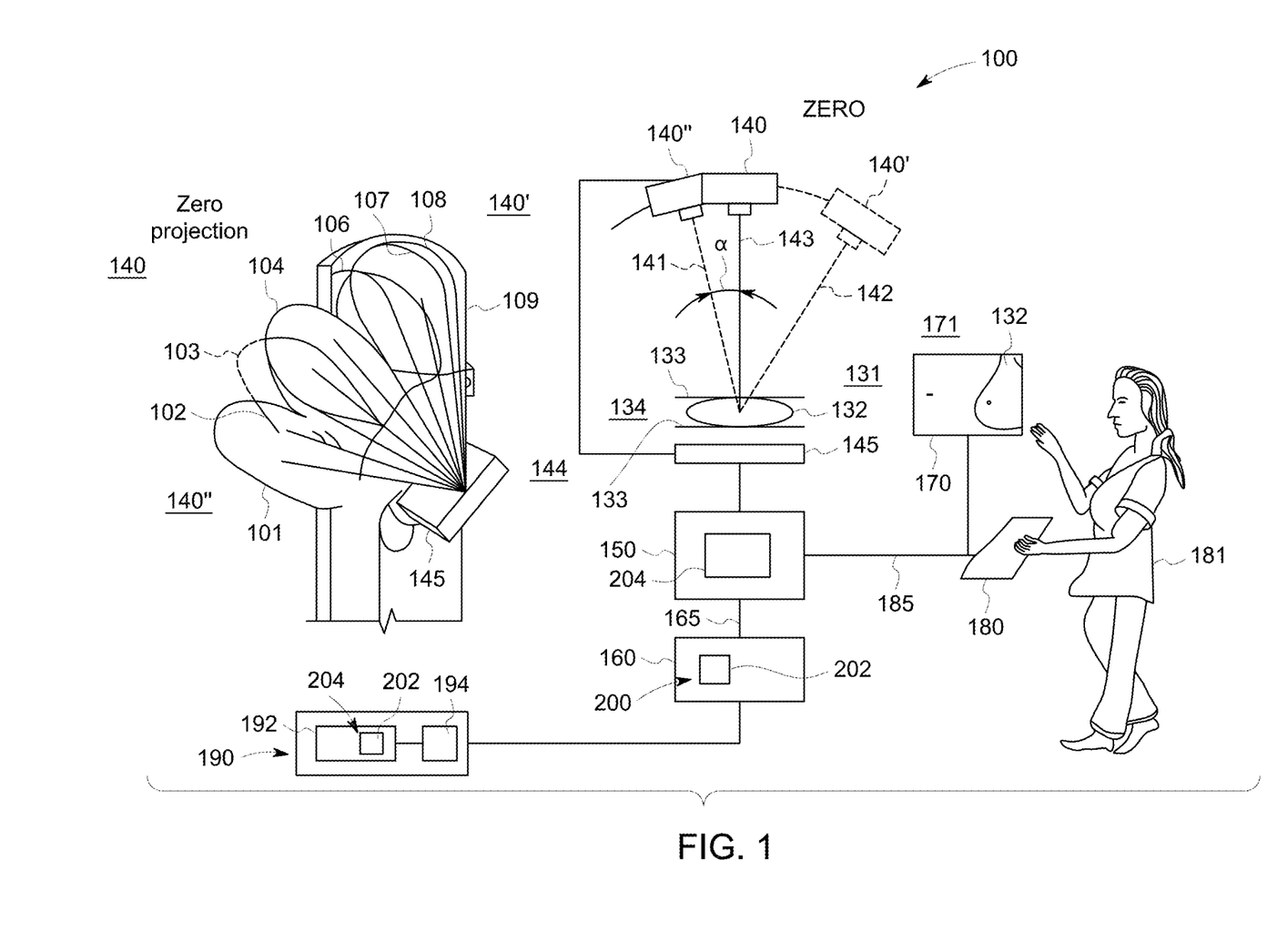
FIG. 1 is a schematic view of an imaging system for use with the automated anomaly detection system in accordance with an exemplary embodiment of the disclosure.

Referring now to FIG. 1, an x-ray imaging system 100, such as that disclosed in U.S. Pat. No. 10,092,262 (the '262 patent), entitled Methods And System For Tomographic Projection Images Enhancement, the entirety of which is expressly incorporated herein by reference for all purposes, may be used to obtain images of an object of interest 132, such as a breast. The system 100 comprises a x-ray beam source 140 facing the detector 145. The x-ray beam source 140 and the detector 145 are connected by an arm 144. Between the detector 145 and the source 140 an object of interest 132 can be placed. In the system illustrated, the x-ray source 140 moves in an arc above a single detector 145. The detector 145 and a plurality of positions of the x-ray source 140' and 140" following an arc (see dashed line) are shown with dashed/solid lines and in a perspective partial view. In the shown arrangement, the detector 145 is fixed at the shown position and only the x-ray source 140 moves. The angle α is a projection angle enclosed by the zero-orientation and any other orientation such as 141 and 142. In this way multiple different views of the breast tissue can be acquired via the at least one x-ray source 140. The projection of lowest α or the projection closest to the zero-orientation is named the central projection or zero projection by approximation.

Still referring to FIG. 1, on the left side is shown a partial perspective view of an imaging system according to an exemplary embodiment of the disclosure comprising a detector 145 and an x-ray source 140. The different positions of the x-ray source 140, 140' and 140" are broadly depicted to illustrate the movement of the x-ray source. There are nine different projection views 101, 102, 102, 103, 104, 106, 107, 108, 109 including the zero projection (105) indicated as straight lines, which all point to the center of the detector 145.

The patient (not shown) is positioned in front of the mammography arm 144. To take for example a known mediolateral oblique (MLO) view, the mammography technologist 181 will set the angle for the desired projection (30 degrees to 60 degrees, wherein 45 degree represents the preferred zero projection shown in the perspective view of FIG. 1). During routine screening mammography, the angled MLO view is preferred over a lateral 90-degree projection because more of the breast tissue can be imaged.

The object of interest 132 shown in display unit 170 is a breast compressed by compression paddles 133, which ensure uniform compression and immobilization of the breast during the radiation exposure for optimal image quality. The breast 132 comprises for example a punctual object 131 as a calcification, which is located in the zero orientation 143, which is perpendicular to the detector 145 plane. The user may review calcifications or other clinical relevant structures for diagnosis. The display depicts a known 2D mammography view, where mainly the middle portion of the breast 132 can be reviewed.

The detector 145 and the x-ray source 140 constitute the acquisition unit, which is connected via a data acquisition line 155 to a processing unit 150. The processing unit 150 comprises for example, one or more computers, one or more processors, microcontrollers, etc., as well as a memory unit 160, which may be connected via an archive line 165. The processing unit 150 can receive the image data from the acquisition unit via the data acquisition line 155 can operate in a known manner to process the image data into projection images associated with the image data obtained at a specified projection view 101-109.

A user can input control signals via the user interface 180. Such signals are transferred from the user interface to the processing unit 150 via the signal line 185. The method and system according to the disclosure enables the user to obtain an enhanced 2D projection image that looks like a known 2D mammogram. Further there is the possibility of displaying stored former 2D mammograms for comparison with the one acquired through the tomosynthesis modality according to the present disclosure. Besides, tomosynthesis images may be reviewed and archived. A CAD system or the user himself can provide 3D marks. A height map of punctual objects or other objects obtained according to an embodiment of the disclosure can be combined with height information provided by 3D marks by a CAD system or indicated by a user through a 3D review system. Further, the user may decide if the 2D/3D full-volume images or other images are archived or not. Alternatively saving and storing of the images may be done automatically.

The memory unit 150 can be integral or separate from the processing unit 150. The memory unit 160 allows storage of data such as the 2D enhanced projection images and tomosynthesis 2D/3D images. In general, the memory unit 160 may comprise a computer-readable medium for example a hard disk or a CD-ROM, diskette, a ROM/RAM memory, DVD, a digital source such as a network or the Internet or any other suitable means. The processing unit 150 is configured to execute program instructions stored in processing unit 150 and/or the memory unit 160, which cause the computer to perform the methods of the disclosure.

Figure 2:
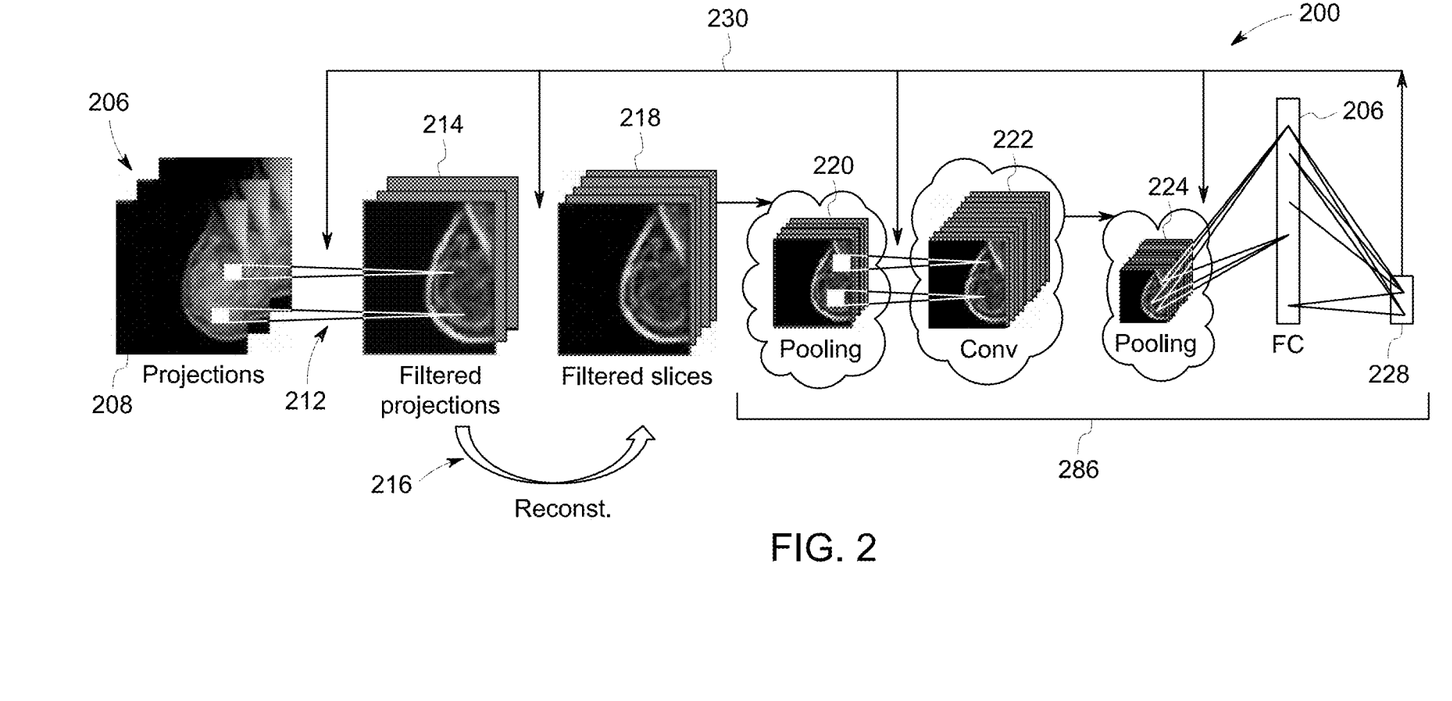
FIG. 2 is a flowchart of the operation of the automated anomaly detection system utilizing 2D projections as the input for the system in accordance with an exemplary embodiment of the disclosure.

Referring now to FIGS. 1-2, the processing unit 150 of the imaging system 100 employs a deep learning neural network 200, such as a convolutional neural network (CNN) 202, functioning as an automatic anomaly/lesion detection system 204. The instructions for operation of the CNN 202 can be stored in memory unit 160 or another memory database (not shown) and can be accessed by the processing unit 150 or other computer or processing unit (not shown) operably connected to processing unit 150. Alternatively, or in addition to the processing unit 150, a separate processing unit 192 can be employed on a remote computing device 190 that includes the CNN 202 and/or memory 194 on which the instructions for the operation of the CNN 202 are stored and which is connected to the imaging system 100 to obtain the data for the 2D enhanced projection images and tomosynthesis 2D/3D images. The system 204 employing the CNN 202 operates according to a number of different embodiments that receive various compact data representation inputs 206 in order to provide the automatic anomaly detection function output from the system 204 in a faster/less computationally intensive manner that also requires a significantly smaller memory footprint for its operation. This benefit is realized due to the reduced complexity and/or number of the inputs 206 provided to the CNN 202, which also can improve the quality of the output/detection results of the CNN 202. The aggregating of the image data input into a smaller number of and/or less complex images, e.g., one or more projection images, enables the CNN 202 to create different forms of the input 206 within the CNN 202, which in turn allows for better location and/or detection of lesions within the images.

In the exemplary embodiment of the operation of the CNN 202 as the anomaly detection system 204 shown in FIG. 2, the compact data representation input 206 takes the form of the 2D projections/projection images 208 originally obtained by the imaging system 100. Once input into the anomaly detection system 204, the CNN 202/system 204 proceeds to analyze the projections 208 by performing or employing a filtering operation and/or convolutional layer 212 on these 2D projections 208. In the first convolution operation 212, the projections 208 are scanned utilizing suitable filters or kernels followed by the application of a selected non-linear activation function, such as the ReLU activation function, to obtain filtered projections 214. In an exemplary embodiment of the filtering operation and/or convolutional layer 212, the filters or kernels applied to the projections 208 can be user-defined, learned by the CNN 202, or a combination thereof. The ability of the CNN 202 to learn the filters/kernels when analyzing the projections 208 can significantly increase the speed of analysis of the projections 208, in conjunction with the reduced complexity of the projections 208.

A reconstruction operation 216 is then performed by the CNN 202/system 204 on the filtered projections 214 utilizing a backprojection process. The backprojection inputs filtered projection and thus outputs filtered slices 218. These can then be run through a pooling layer 220 that applies a suitable downsampling operation, such as a max pooling operation, to the filtered slices 218. After the pooling layer 220, a number of additional convolutional layers 222 and pooling layers 224 can be applied to the image data to provide enhanced anomaly detection functionality from the system 204. The CNN 202 can also employ one or more fully connected layers 226 and associated weighting factors after the final pooling layer 224 which, optionally in conjunction with the pooling layer(s) 220, additional convolutional layer(s) 222 and pooling layer(s) 224, constitute a detection operation 286, in order to optimize the anomaly detection in the image data prior to providing the anomaly detection output 228. After generation of the output 228 in the learning phase for the operation of the system 204, a backpropagation process 230 can be employed by the CNN 202 to enable the CNN 202 to learn, adjust and/or optimize the filters/kernels and any weighting factors applied by the CNN 202 at each layer back to the projections 208 supplied to and/or created from the input image data, which can also be employed in any of the embodiments of the system 204 and its operation in this disclosure.

With regard to the operation of the reconstruction process/operation or layer 216, a filtered backprojection can be performed using the geometry of the central projection 208 (the one that is perpendicular to the detector) as described in the '262 patent. In this implementation, features are naturally aligned avoiding the operator to perform reprojection and thus simplifying the network architecture.

Figure 3:
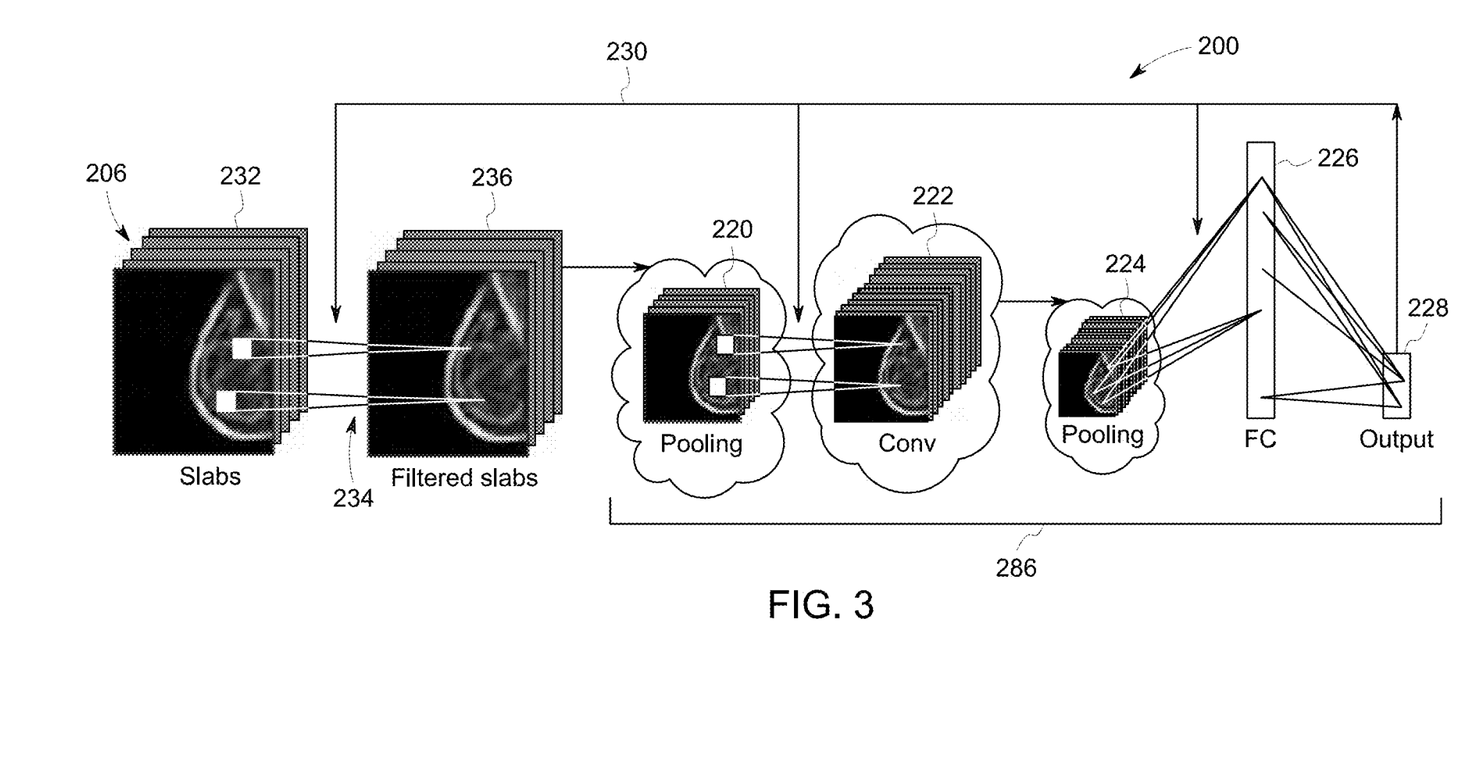
FIG. 3 is a flowchart of the operation of the automated anomaly detection system utilizing slabs as the input for the system in accordance with an exemplary embodiment of the disclosure.

Referring now to FIG. 3, the CNN 202 can alternatively use slabs 232 as the compact data representation input 206 for the automatic anomaly detection system 204. The slabs 232 are formed by the processing unit 150 as 2D/3D thick slice reconstructions of the 2D projection images 208 that aggregate the information contained in several consecutive planes or slices to provide the two main benefits of allowing a regrouping of calcifications that may be spread over several consecutive planes/thicknesses to make available a clinical cluster information, and allowing a reduction of the data, by a factor depending on slabs under-sampling as compared to slices sampling, as disclosed the '264 application.

Per the first benefit, when dealing with a task of automatic lesion detection using the CNN 202 in the system 204, better calcifications cluster detection performance is expected to result with a CNN 202 that processes slabs 232 rather than individual planes or slices. There is also a significant reduction of redundant detections for the same lesion when spread over several consecutive slices 218, as these lesions will be almost wholly contained within the single slab 232. Per the second benefit, we expect a computation time and memory footprint reduction when processing slabs 232 as a direct result of the fewer number of slabs 232 to be processed by the CNN 202. Thus, a direct option for the operation of the system 204 as shown in the exemplary embodiment of FIG. 3 includes feeding the CNN 202 with precomputed slabs 232 as the compact data representation input 206 on which is performed a filtering operation and/or convolutional layer 234 utilizing suitable filters or kernels, and a selected non-linear activation function, such as ReLU, to obtain filtered slabs 236 as the outputs/feature map from the layer 234. Similarly to the filtering operation and/or convolutional layer 212, in an exemplary embodiment of the filtering operation and/or convolutional layer 234, the filters or kernels applied to the slabs 232 can be user-defined, learned by the CNN 202, or a combination thereof. The ability of the CNN 202 to learn the filters/kernels when analyzing the slabs 232 can significantly increase the speed of analysis of the slabs 232. Similar to the prior system 204 illustrated in FIG. 2, the filtered slabs 236 can then be run through a pooling layer 220 that applies a suitable downsampling operation, such as a max pooling operation, to the filtered slabs 236. After the pooling layer 220, a number of additional convolutional layers 222 and pooling layers 224 can be applied to the image data to provide enhanced anomaly detection functionality from the system 204. The CNN 202 can also employ one or more fully connected layers 226 and associated weighting factors after the final pooling layer 224, which, optionally in conjunction with the pooling layer(s) 220, additional convolutional layer(s) 222 and pooling layer(s) 224, constitute a detection operation 286, in order to optimize the anomaly detection in the image data prior to providing the output 228. After generation of the output 228, a backpropagation process 230 can be employed by the CNN 202 to enable the CNN 202 to learn, adjust and/or optimize the filters/kernels and any weighting factors applied to the image data supplied to and/or created from the input image data in any one or more layers of the CNN 202.

Figure 4:
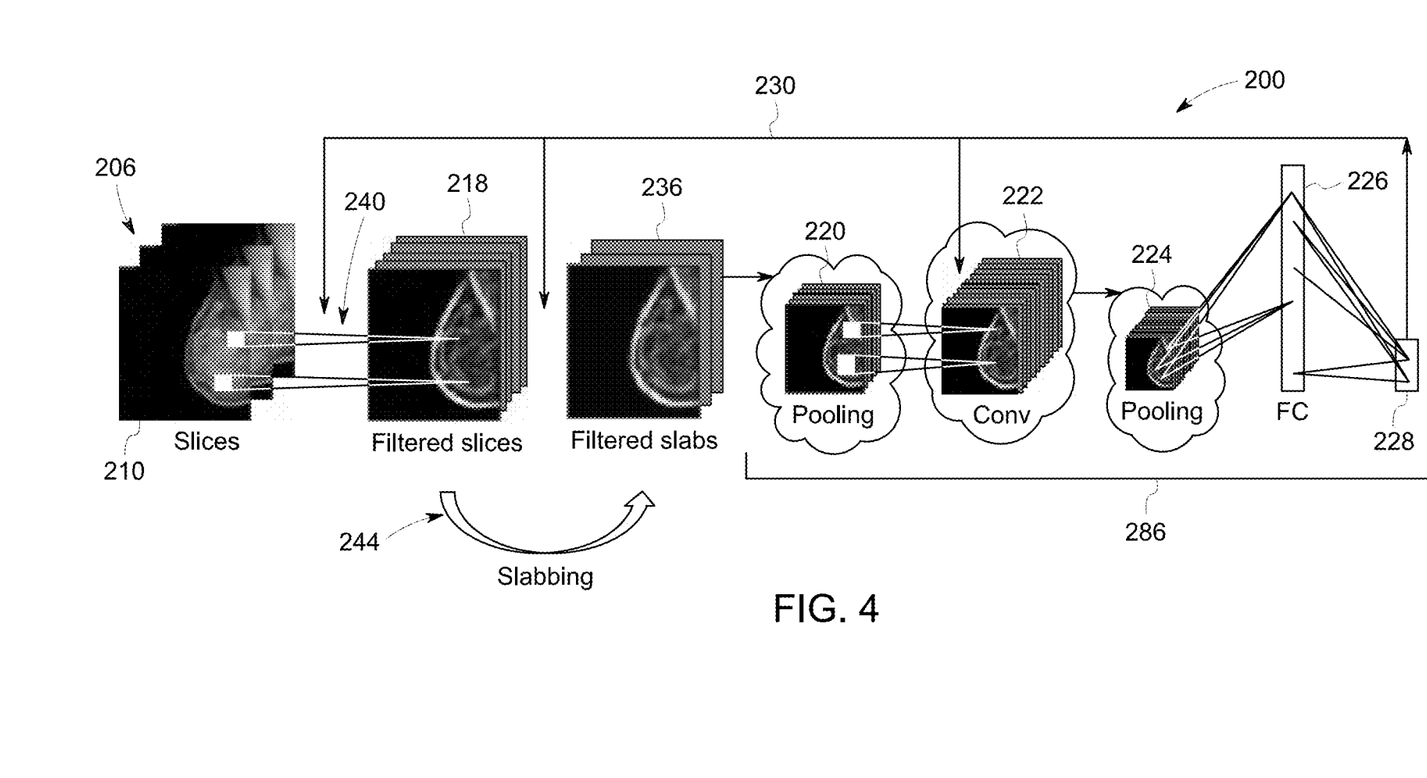
FIG. 4 is a flowchart of the operation of the automated anomaly detection system utilizing slices as the input for the system and optionally performing slabbing in a first layer of the CNN in accordance with an exemplary embodiment of the disclosure.

Referring now to the exemplary embodiment of FIG. 4, still another alternative for the compact data representation input 206 supplied to the CNN 202 are precomputed slices 210 produced by the processing unit 150 from the projections 208. The slices 210 are run through a first filtering operation and/or convolutional layer 240 in which the slices 210 are scanned utilizing suitable filters or kernels followed by the application of a selected non-linear activation function, such as the ReLU activation function, to obtain filtered slices 218. Similarly to the filtering operation 212, in an exemplary embodiment of the first filtering operation 240, the filters or kernels applied to the slices 210 can be user-defined, learned by the CNN 202, or a combination thereof. The ability of the CNN 202 to learn the filters/kernels when analyzing the slices 218 can significantly increase the speed of analysis of the slices 210. A slabbing operation 244 can then optionally be performed on the filtered slices 218 to obtain filtered slabs 236. The process 244 can be fixed using a 3D pooling or a more clinically relevant operator as disclosed in US Patent Application Publication No. US 2012/0121064 (the '264 application), entitled Procedure For Processing Patient Radiological Images, the entirely of which is expressly incorporated herein by reference for all purposes. This operator might embed a reprojection step onto a central projection 208 to align features because of the conic geometry of the acquisition Similar to prior embodiments, either the filtered slices 218 or the filtered slabs 236 can then be run through a pooling layer 220, a number of additional convolutional layers 222 and pooling layers 224 and one or more fully connected layers 226 and associated weighting factors after the final pooling layer 224, which, optionally on conjunction with the pooling layer(s) 220, additional convolutional layer (s) 222 and pooling layer(s) 224, constitute a detection operation 286, in order to optimize the anomaly detection in the image data prior to providing the output 228. After generation of the output 228, a backpropagation process 230 similar to that described with regard to previous embodiments can be employed to learn, adjust and/or optimize the filters/kernels and any weighting factors applied to the image data in any one or more layers of the CNN 202. In particular, in this embodiment, the learning process shall backpropagate the gradients/kernels through the slabbing process back to the convolutional filters/kernels applied on the slices 210.

Figure 5:
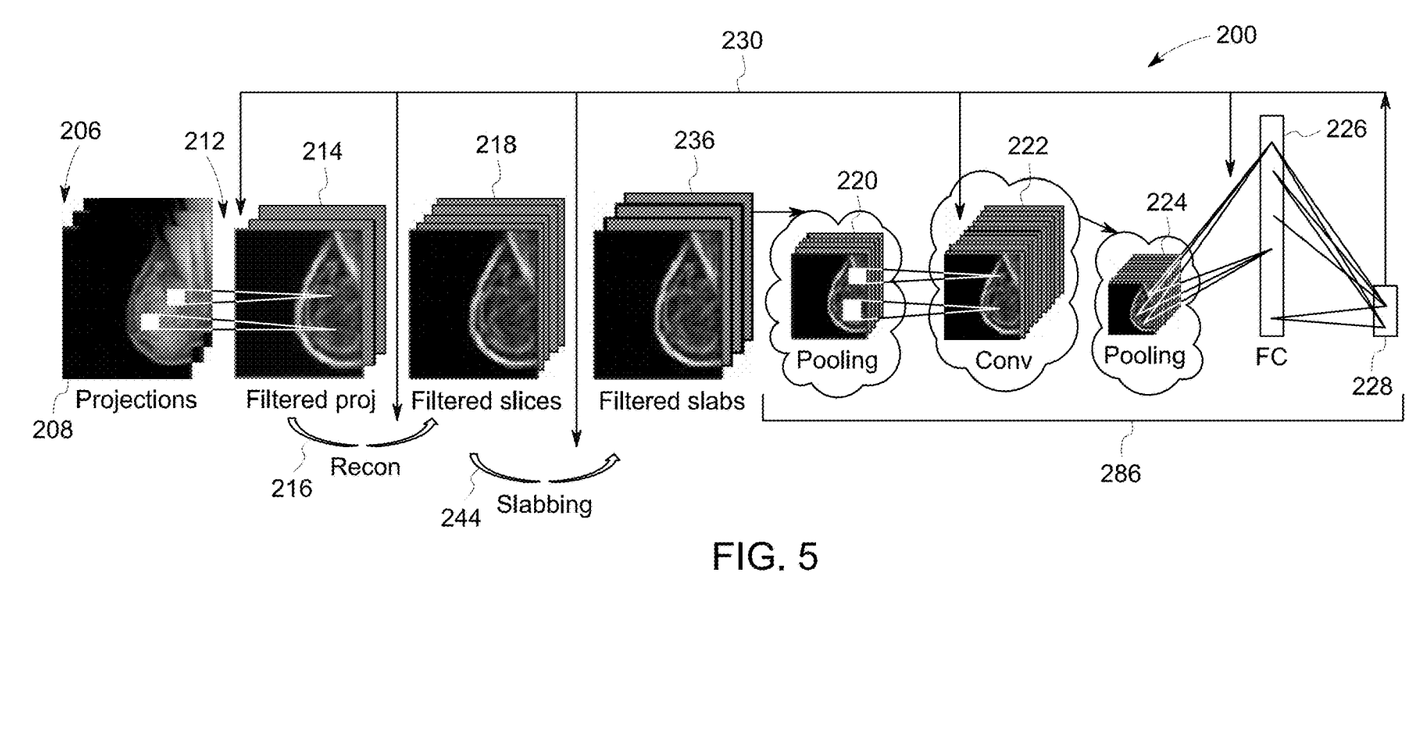
FIG. 5 is a flowchart of the operation of the automated anomaly detection system utilizing 2D projections as the input for the system and performing reconstruction and slabbing in initial layers of the CNN in accordance with an exemplary embodiment of the disclosure.

Referring now to the alternative exemplary embodiment of FIG. 5, which is similar to the embodiments of FIGS. 2-4, the compact data representation input 206 supplied to the CNN 202 are the projections 208. The projections 208 are initially run through a first filtering operation/convolution layer 212 by the CNN 202 to obtain filtered projections 214. A reconstruction operation 216 is then performed by the CNN 202 on the filtered projections 214 to obtain filtered slices 218 as an outputs/feature maps of the reconstruction operation or layer 216 similar to the embodiment of FIG. 2. In addition, similar to the prior embodiment of FIG. 4, a slabbing operation 244 is then performed by the CNN 202 on the filtered slices 218, to obtain filtered slabs 236 as an outputs/feature maps of the slabbing layer 244. These filtered slabs 236 are subsequently run through a pooling layer 220, a number of additional convolutional layers 222 and pooling layers 224 and one or more fully connected layers 226 and associated weighting factors after the final pooling layer 224, which, optionally in conjunction with the pooling layer(s) 220, additional convolutional layer(s) 222 and pooling layer(s) 224, constitute a detection operation 286, in order to optimize the anomaly detection in the image data prior to providing the output 228. After generation of the output 228, a backpropagation process 230 similar to that described with respect to any previous embodiment can be employed to learn, adjust and/or optimize the filters/kernels and any weighting factors applied to the image data in any one or more layers of the CNN 202. In particular, in this embodiment, the learning process shall backpropagate the gradients/kernels through the reconstruction and slabbing processes back to the convolutional filters/kernels applied on the projections 208.

With regard to any of the embodiments in FIGS. 3-5, the slab thickness may be tailored to an average lesion size in order to aggregate the relevant information for a detection task purpose and/or for a presentation purpose. Also, similarly to the reconstruction process, the slabbing process in any of the embodiments can be fixed using a 3D pooling or a more clinically relevant operator as disclosed in the '264 application. This operator might embed a reprojection step onto a central projection 208 or onto the central slice composing the slab to align features because of the conic geometry of the acquisition. In a preferred embodiment, a filtered backprojection is performed in 216 using the geometry of the central projection 208 (the one that is perpendicular to the detector) as described in the '262 patent. In this implementation, features are naturally aligned avoiding the operator to perform complex reprojection and thus simplifying the network architecture.

Figure 6:
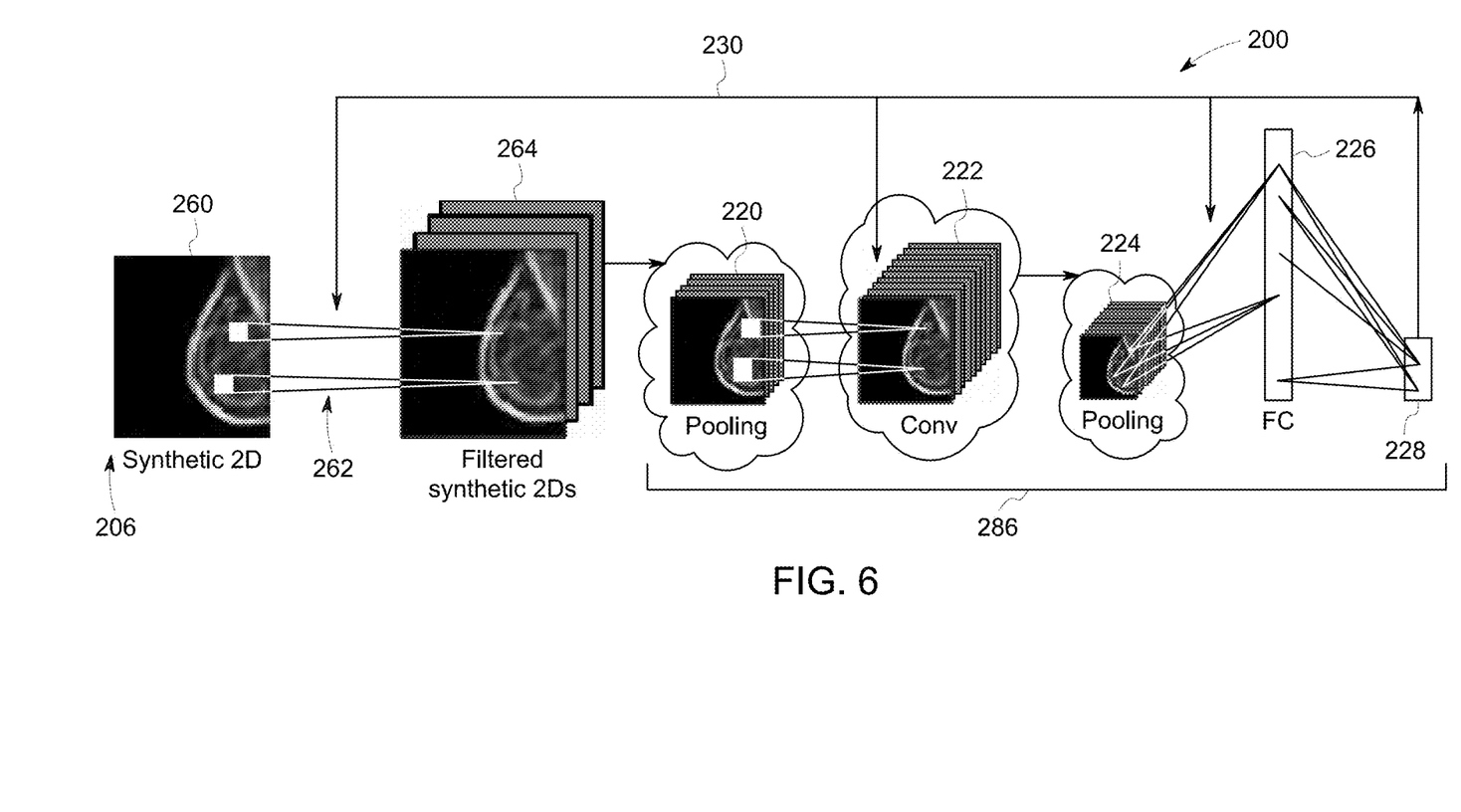
FIG. 6 is a flowchart of the operation of the automated anomaly detection system utilizing a synthetic 2D image as the input for the system in accordance with an exemplary embodiment of the disclosure

Referring now to the alternative embodiment of FIG. 6, the compact representation data input 206 for the CNN 202 forming the automated anomaly detection system 204 is a synthetic 2D image 260. The synthetic 2D image 260 is a representation that aggregates the information contained in the entire set of projections 208/slices 218 into a single image 260. The synthetic 2D image 260 provides the additional benefit similar to a slab of regrouping calcifications that may be spread over multiple slices, resulting in improved clinical cluster information. As a result, the use of the synthetic 2D image 260 as the compact representation data input 206 provides a significant computation time reduction and memory footprint reduction, but at the expense of 3D localization. This tradeoff can be relevant for certain tasks as for the detection of large clusters of calcifications. The boundaries of this lesions are indeed often not well-defined making 3D localization difficult.

In FIG. 6, the input 206 to the CNN 202 is a precomputed synthetic 2D image 260. The synthetic 2D image 260 is through a filtering operation and/or convolutional layer 262 in which the image 260 scanned utilizing suitable filters or kernels followed by the application of a selected non-linear activation function, such as the ReLU activation function, to obtain filtered synthetic 2D image(s) 264. Similarly to the filtering operation 212, in an exemplary embodiment of the filtering operation 262, the filters or kernels applied to the synthetic 2D image 260 can be user-defined, learned by the CNN 202, or a combination thereof. Also similar to prior embodiments, the filtered synthetic 2D images 264 can then be run through a pooling layer 220, a number of additional convolutional layers 222 and pooling layers 224 and one or more fully connected layers 226 and associated weighting factors after the final pooling layer 224, which, optionally in conjunction with the pooling layer(s) 220, additional convolutional layer(s) 222 and pooling layer(s) 224, constitute a detection operation 286, in order to optimize the anomaly detection in the image data prior to providing the output 228. After generation of the output 228, a backpropagation process 230 can be employed to learn, adjust and/or optimize the filters/kernels and any weighting factors applied to the image data in any one or more layers of the CNN 202. In particular, in this embodiment, the learning process shall backpropagate the gradients/kernels back to the convolutional filters/kernels applied on the synthetic 2D image 260.

Figure 7:
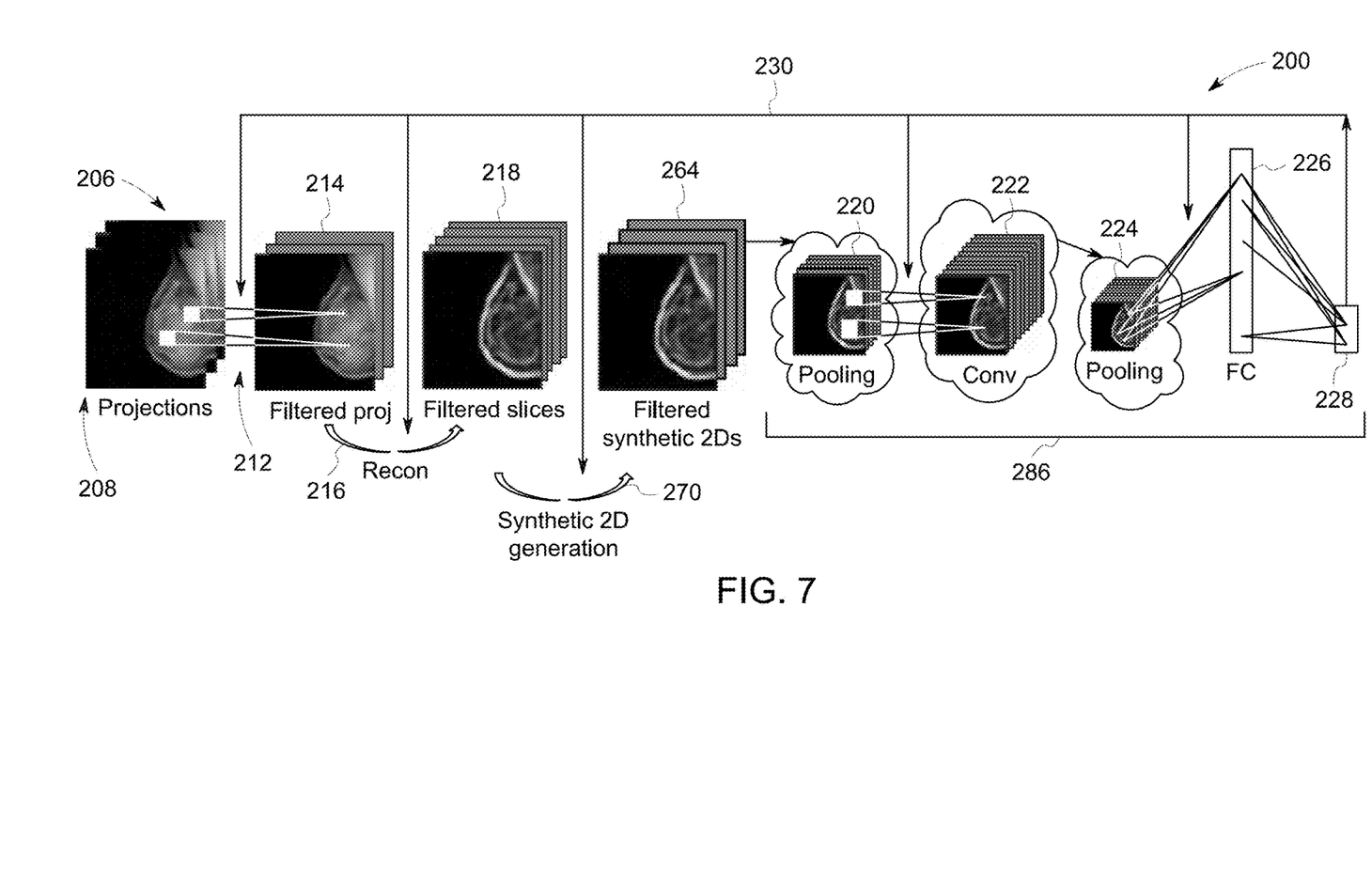
FIG. 7 is a flowchart of the operation of the automated anomaly detection system utilizing 2D projections as the input for the system and performing reconstruction and synthetic 2D image generation in initial layers of the CNN in accordance with an exemplary embodiment of the disclosure.

Looking now at the exemplary embodiment of FIG. 7, similar to the embodiment of FIG. 5, the compact data representation input 206 supplied to the CNN 202 are the projections 208. The projections 208 are initially run through a first convolution layer or filtering 212 to obtain filtered projections 214. A reconstruction operation 216 is then performed on the filtered projections 214 to obtain filtered slices 218 as an outputs/feature maps of the reconstruction layer 216 similar to the embodiment of FIG. 5. A synthetic 2D generation image generation operation 270 is then performed on the filtered slices 218, to obtain filtered synthetic 2D images 264 as an outputs/feature maps of the synthetic 2D generation layer 270. These filtered synthetic images 264 are subsequently run through a pooling layer 220, a number of additional convolutional layers 222 and pooling layers 224 and one or more fully connected layers 226 and associated weighting factors after the final pooling layer 224, which, optionally in conjunction with the pooling layer(s) 220, additional convolutional layer(s) 222 and pooling layer(s) 224, constitute a detection operation 286, in order to optimize the anomaly detection in the image data prior to providing the output 228. After generation of the output 228, a backpropagation process 230 can be employed to learn, adjust and/or optimize the filters/kernels and any weighting factors applied to the image data in any one or more of the layers of the CNN 202. In particular, in this embodiment, the learning process shall backpropagate in process 230 the gradients/kernels through the reconstruction and synthetic 2D processes back to the convolutional filters/kernels applied on the projections 208. In this embodiment, the synthetic 2D generation process can be fixed using a MIP (Maximum Intensity Projection) operator or a more clinically relevant operator as described in the '262 patent. In another embodiment, the synthetic 2D generation process might embed some parameters to be learned during the network training phase. In a preferred embodiment, a filtered backprojection is performed in 216 using the geometry of the central projection 208 (the one that is perpendicular to the detector) as described in the '262 patent. In this implementation, features are naturally aligned avoiding the operator to perform complex reprojection and thus simplifying the network architecture.

Figure 8:
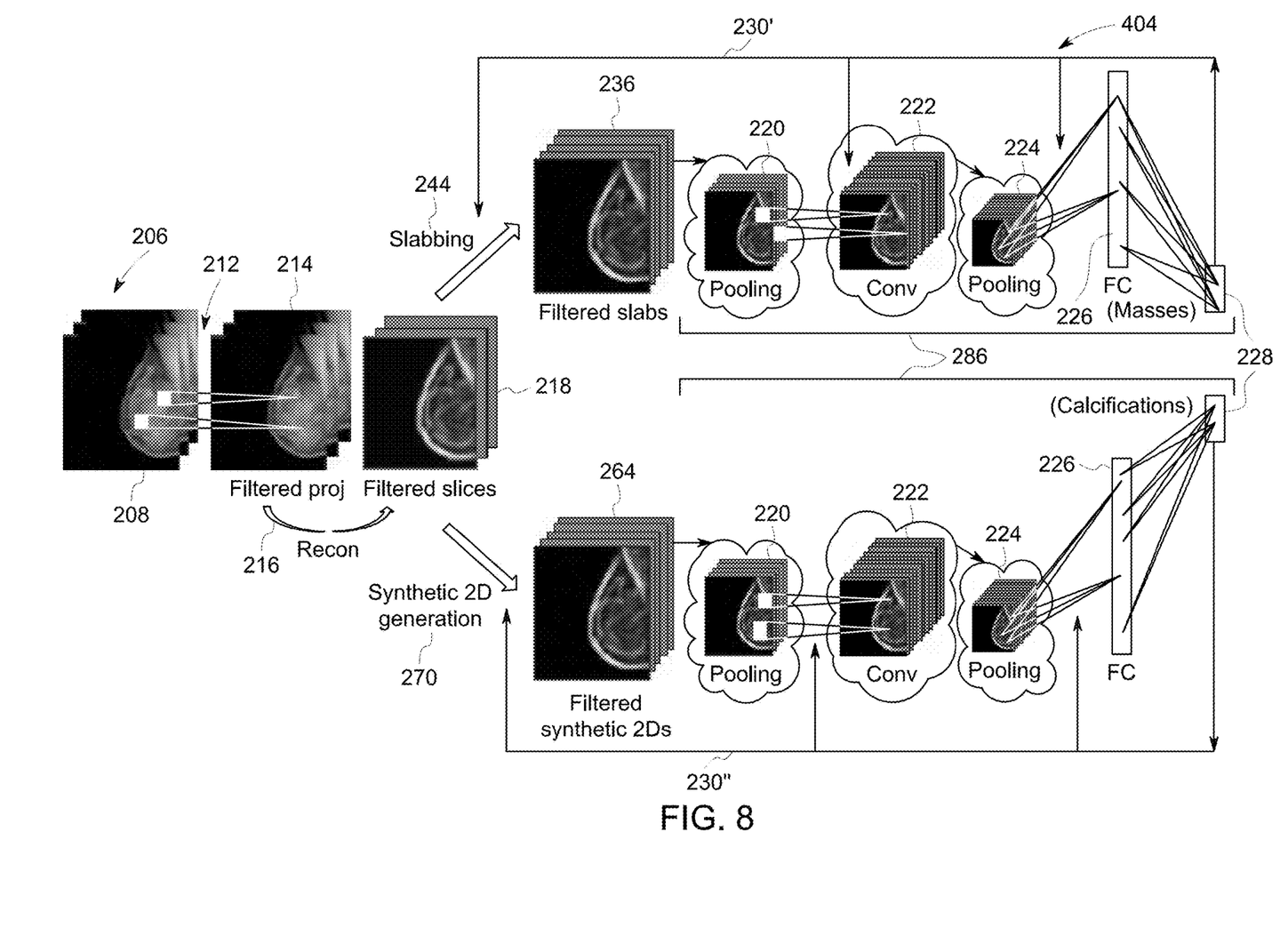
FIG. 8 is a flowchart of the operation of the automated anomaly detection system utilizing 2D projections as the input for the system and performing separate slabbing and synthetic 2D image generation in different processes of the CNN in accordance with an exemplary embodiment of the disclosure.

From a clinical standpoint, some radiologists already use two separate representations obtained from the same original projection data in their daily practice where they locate masses in the 3D volume and calcification clusters in the synthetic 2D image as result of the benefits of reduced tissue superimposition in the DBT 3D volume, and the clear representation of calcification clusters in a 2D image. In one exemplary embodiment, a first CNN 202 from FIGS. 2 to 5 can be employed for the detection of a first type of lesion, e.g., masses, and a second CNN 202 from FIG. 6 or 7 can be employed in parallel for detection of a second type of lesion, e.g., calcification clusters. However, referring now to FIG. 8, a multi-task/multi-representation automated anomaly detection system 404 utilizing the CNN 202 is illustrated which leverage both the generation slabs and synthetic 2D representations to reduce the computational load for the CNN 202 and to reduce the memory footprint required for operation of the CNN 202. In the system 404, after employing a filtering operation/convolutional layer 212 on the projection 208 to obtain filtered projections 214, the CNN 202 employs a reconstruction operation 216 to generate filtered slices 218 from the filtered projections 214. Subsequently, utilizing separate network branches, a first branch 272 for a slabbing operation/layer 244 and a second branch 274 for a synthetic 2D generation operation/layer 270, the CNN 202 generates filtered slabs 236 and filtered synthetic 2D images 264 from the filtered slices 218. The generated filtered slabs 236 and filtered synthetic 2D images 264 are each subsequently run through corresponding further pooling layers 220,224, convolutional layers 222 and one or more fully connected layers 226 that in some combination form detection operations 286 for both first and second lesion types, to optimize the anomaly detection in the image data prior to providing the outputs 228. The loss function to be minimized in the backpropagation would be composed of two sub-losses 230'230", one for the slabs branch 272 and one for synthetic 2D branch 274. The depth/number of layers 222 of each branch 272,274 can be different as the lesions to be detected within the images of each branch 272,274 are of different sizes, e.g., cm unit for the first lesion type, e.g., masses (slab branch 272) vs micrometers for the second lesion type, e.g., calcifications (synthetic 2D branch 274).

Figure 9:
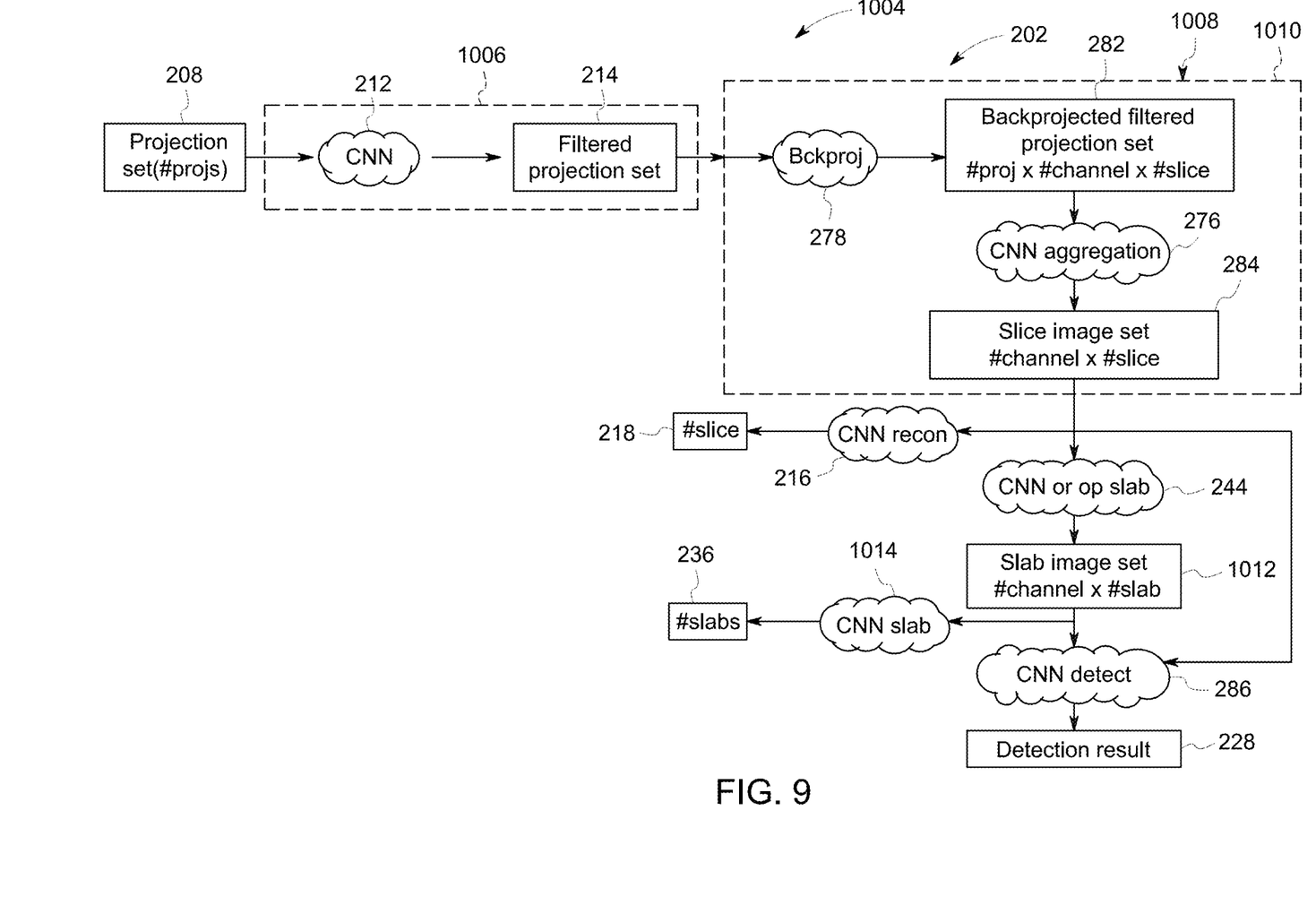
FIG. 9 is a flowchart of the operation of the automated anomaly detection system utilizing 2D projections as the input for the system with an embedded backprojection operator for outputting both reconstructed slice and slabs from the CNN along with the detection result in accordance with an exemplary embodiment of the disclosure.

Looking now at FIG. 9, the computationally intensive reconstruction process/convolution operation layer 216 is employed in a visualization and detection system 1004 to provide outputs for each of the visualization of the object of interest 132 in addition to the detection of anomalies/lesions within the object of interest 132 as opposed to employing separate systems for each of the anomaly detection and visualization of the object 132. For example, implementing the CNN 202 of any of the embodiments of FIGS. 2-8, the CNN 202 can be operated in a manner in which the 2D projections 208 used as input 206 are processed through the first filtering operation/convolution layer 212, to form the 2D filtered projection set 214 including filtered projection images in a 2D processing section 1006 of the system 1004. This 2D filtered projections/projection set 214 is then applied as an input to a 3D processing section 1008 of the system 1004. The 3D processing section 1008 employs a reconstruction operation 1010 employed as one or more layers of the CNN 202 which includes as a first step a backprojection operation 278 which provides as an output a set of backprojected filtered projections 282. This set 282 is subsequently run through an aggregation operation/convolution operation layer 276 that provides a slice image set 284 in any of a manner of known processes, such as a summation of the filtered slices in the set 282 for each channel for a simple example, or more complex non-linear operations such as one or more layers of a full CNN. The set 284 can then subsequently be processed in a number of distinct manners by the system 1004 in order to provide outputs for both the visualization and detection functions of the system 1004. In the illustrated exemplary embodiment of the system 1004 shown in FIG. 9, the image set 284 can be processed through each of one or more layers of a CNN 216 as described previously to generate viewable slices 218 that are typically slices with one channel per slice like conventional reconstructed DBT datasets, a slabbing operation layer 244 to form a slab image set 1012 followed by one or more layers of another CNN 1014 as described previously to generate viewable slabs 236 that are typically slabs with one channel per slab like conventional reconstructed DBT datasets, and a detection operation(s) layer(s) 286 as described previously to generate the automatic anomaly detection output 228 from one or both of the slice image set 284 and the slab image set 1012. In this system 1004, the output of the 3D processing section 1008 can be utilized to generate each of the viewable slices 218 and slabs 236, as well as used for the analysis performed by the detection operation 286 of the CNN 202, such that the anomaly detection output 228 can be presented in conjunction with the selected slice 218 or slab 236 for review by an individual, thereby utilizing the computationally intensive 3D processing section 1008 to provide output for both each of visualization and detection operations of the system 1004. In addition, the viewable slices 218 and/or slabs 236 can be utilized as an input to some type of reconstruction post processing, such as iterative reconstruction, as is often the case.

Finally, it is also to be understood that the system 100 may include the necessary computer, electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the system may include at least one processor/processing unit/computer and system memory/data storage structures, which may include random access memory (RAM) and read-only memory (ROM). The at least one processor of the system may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application(s)/algorithm(s) that adapts the computer/controller to perform the methods disclosed herein may be read into a main memory of the at least one processor from a computer-readable medium. The term "computer-readable medium", as used herein, refers to any medium that provides or participates in providing instructions to the at least one processor of the system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is understood that the aforementioned compositions, apparatuses and methods of this disclosure are not limited to the particular embodiments and methodology, as these may vary. It is also understood that the terminology used herein is for the purpose of describing particular exemplary embodiments only, and is not intended to limit the scope of the present disclosure which will be limited only by the appended claims.

We claim:

1. A method for detecting an anomaly in one or more images obtained from an X-ray imaging procedure on an object, the method comprising the steps of:
    a. providing a computing system on which an automatic anomaly detection system is provided, the anomaly detection system comprising:
        i. a processing unit configured to receive and process projection images, the processing unit including a convolutional neural network;
        ii. an electronic information storage device operably connected to the processing unit and containing operational instructions for the convolutional neural network; and
    b. supplying a compact data representation input of the projection images of an object of interest to the automatic anomaly detection system;
    c. analyzing the compact data representation input with the automatic anomaly detection system in at least one layer of the convolutional neural network to obtain an anomaly detection result; and
    d. outputting an anomaly detection result from the automatic anomaly detection system,
    wherein filters for the at least one layer of the convolutional neural network employed on the compact data representation input are at least partially learned by the automatic anomaly detection system.

2. The method of claim 1, wherein the at least one layer of the convolutional neural network is one of a filtering operation, a reconstruction operation, a slabbing operation, a 2D synthetic image generation and combinations thereof.

3. The method of claim 1, wherein the compact data representation input is the set of projection images.

4. The method of claim 3, wherein the step of analyzing the compact data representation input comprises the steps of:
    a. performing a filtering operation on the set of projection images to form filtered projection images;

b. performing a reconstruction operation on the filtered projection images to form filtered slices.

5. The method of claim 3, wherein the step of analyzing the compact data representation input comprises the steps of:
   a. performing a filtering operation on the set of projection images to form filtered projection images;
   b. performing a reconstruction operation on the filtered projection images to form filtered slices; and
   c. performing a slabbing operation on the filtered slices to obtain filtered slabs.

6. The method of claim 3, wherein the step of analyzing the compact data representation input comprises the steps of:
   a. performing a filtering operation on the set of projection images to form filtered projection images;
   b. performing a reconstruction operation on the filtered projection images to form filtered slices;
   c. performing a slabbing operation on the filtered slices to obtain filtered slabs; and
   d. performing a synthetic 2D image generation operation on the filtered slices to obtain filtered 2D synthetic images.

7. The method of claim 6, further comprising the steps of:
   a. performing one or more detection operations on the filtered slabs to obtain a first lesion type output; and
   b. performing one or more detection convolution operations on the filtered 2D synthetic images to obtain a second lesion type output.

8. The method of claim 3, wherein the step of analyzing the compact data representation input comprises the steps of:
   a. performing a filtering operation on the set of projection images to form filtered projection images;
   b. performing a reconstruction operation on the filtered projection images to form filtered slices; and
   c. performing a synthetic 2D image generation operation on the filtered slices to obtain filtered 2D synthetic images.

9. The method of claim 3, wherein the step of analyzing the compact data representation input further comprises the steps of:
   a. performing a filtering operation on the set of projection images to form filtered projection images;
   b. performing a backprojection on the filtered projection images to form a backprojected filtered projection set;
   c. performing an aggregation operation on the filtered backprojected filtered projection set to form a slice image set;
   d. performing at least one of:
      i. a reconstruction operation on the slice image set to form one or more viewable slices,
      ii. a slabbing operation on the slice image set to form a slab image set and a convolutional operation on the slab image set to form one or more viewable slabs, or
      iii. combinations thereof;
   e. performing a detection operation on the slice image set or slab image set to form an anomaly detection result; and
   f. outputting the one or more viewable slices, the one or more viewable slabs, and combinations thereof in conjunction with the anomaly detection result.

10. The method of claim 1, wherein the compact data representation input is a set of precomputed synthetic 2D image and further comprises a step of performing a filtering convolution operation on a synthetic 2D images to obtain filtered synthetic 2D images.

11. The method of claim 1, wherein the compact data representation input is a set of precomputed slices obtained from the projection images.

12. The method of claim 11, wherein the step of analyzing the compact data representation input comprises the steps of:
   a. performing a filtering operation on the set of precomputed slices to form filtered slices; and
   b. performing a slabbing operation on the filtered slices to form filtered slabs.

13. The method of claim 1, wherein the compact data representation input is a set of precomputed slabs and further comprises a step of performing a filtering operation on the set of slabs to form filtered slabs.

14. An X-ray imaging system comprising:
   a. an X-ray source configured to emit radiation beams towards an object;
   b. an X-ray detector movably aligned with the X-ray source to receive the radiation beams from the X-ray source and generate image data;
   c. a processing unit operably connected to the X-ray source and the X-ray detector to control the movement and operation of the X-ray source and X-ray detector, the processing unit configured to receive and process image data from the X-ray detector to form projection images;
   d. a display operably connected to the processing unit for presenting information to a user;
   e. a user interface operably connected to the processing unit to enable user input to the processing unit;
   f. an automatic anomaly detection system operably connected to the controller; and
   g. an electronic information storage device operably connected to the processing unit,
   wherein the automatic anomaly detection system is formed of a convolutional neural network having and operational instructions contained on the storage device to be accessed by the processing unit, the automatic anomaly detection system configured to receive a compact data representation input of the projection images and to analyze the compact data representation input to obtain an anomaly detection result, and wherein filters for the at least one layer of the convolutional neural network employed by the automatic anomaly detection system on the compact data representation are at least partially learned by the automatic anomaly detection system.

15. The method of claim 14, wherein the at least one layer of the convolutional neural network is one of a filtering operation, a reconstruction operation, a slabbing operation, a 2D synthetic image generation and combinations thereof.

16. The X-ray imaging system of claim 14, wherein the compact data representation input is the set of projection images.

17. The X-ray imaging system of claim 16, wherein the automatic anomaly detection system is configured to analyze the compact data representation input by performing a filtering operation on the set of projection images to form filtered projection images, and performing a reconstruction operation on the filtered projection images to form filtered slices.

18. The X-ray imaging system of claim 17, wherein the automatic anomaly detection system is configured to analyze the compact data representation input by performing a slabbing operation on the filtered slices to obtain filtered slabs.

19. The X-ray imaging system of claim 17, wherein the automatic anomaly detection system is configured to analyze the compact data representation input by performing a synthetic 2D image generation operation on the filtered slices to obtain filtered 2D synthetic images.

20. The X-ray imaging system of claim 17, wherein the automatic anomaly detection system is configured to:
   a. analyze the compact data representation input by:
      i. performing a slabbing operation on the filtered slices to obtain filtered slabs; and
      ii. performing a synthetic 2D image generation operation on the filtered slices to obtain filtered 2D synthetic image; and
   b. perform one or more detection operations on the filtered slabs to obtain a first lesion type output; and
   c. perform one or more detection operations on the filtered synthetic 2D to obtain a second lesion type output.

21. The X-ray imaging system of claim 16, wherein the automatic anomaly detection system is configured to:
   a. perform a filtering operation on the set of projection images to form filtered projection images;
   b. perform a backprojection on the filtered projection images to form filtered slices;
   c. perform an aggregation operation on the filtered slices to form an 3D volume image set;
   d. perform at least one of a reconstruction operation to form a viewable slice volume from the 3D volume image set, and a slabbing operation to form a viewable slab volume from the 3D volume image set;
   e. perform a detection operation on the 3D volume image set to form an anomaly detection result; and
   f. output the viewable slices, viewable slabs, and combinations thereof in conjunction with the anomaly detection result on the display.

* * * * *